United States Patent

Beregi et al.

[11] 4,064,245
[45] Dec. 20, 1977

[54] N-PHENOXYPHENYL-PIPERAZINES

[75] Inventors: Laszlo Beregi, Boulogne; Pierre Hugon, Rueil-Malmison; Jacques Duhault, Chatou; Michelle Boulanger, Marly-le-Roi, all of France

[73] Assignee: Science Union et Cie, Societe Francaise de Recherche Medicale, Suresnes, France

[21] Appl. No.: 705,330

[22] Filed: July 14, 1976

[30] Foreign Application Priority Data

July 21, 1975 United Kingdom ............... 30392/75

[51] Int. Cl.² ................. C07D 295/08; A61K 31/495
[52] U.S. Cl. ............................ 424/250; 260/268 PH
[58] Field of Search ................. 260/268 PH; 424/250

Primary Examiner—Paul M. Coughlan, Jr.
Assistant Examiner—Jose Tovar

Attorney, Agent, or Firm—Behr & Woodbridge

[57] ABSTRACT

Phenoxy compounds of the formula:

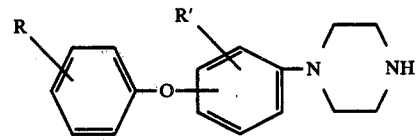

wherein R and R', which are the same or different, are hydrogen, halogen, lower alkyl, lower alkoxy, lower alkylthio, nitro, trifluoromethyl, trifluoromethylthio, trifluoromethoxy, lower alkoxy-carbonyl or dimethylsulfamoyl.

These compounds are used as medicines especially in the treatment of glucid — and lipid — metabolism disorders.

8 Claims, No Drawings

N-PHENOXYPHENYL-PIPERAZINES

The present invention provides phenoxy compounds of the formula I:

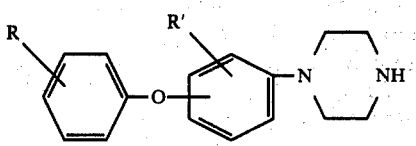

wherein R and R', which are the same or different, are each selected from the group consisting of a hydrogen atom, halogen atoms, alkyl, alkoxy and alkylthio radicals each having from 1 to 5 carbon atoms inclusive, nitro, trifluoromethyl, trifluoromethylthio, trifluoromethoxy, alkoxycarbonyl wherein the alkoxy group has from 1 to 5 carbon atoms inclusive and dimethylsulfamoyl radicals.

The halogen atoms represented by R and R' may be, for example fluorine, chlorine or bromine atoms; the alkyl groups may be, for example methyl, ethyl, propyl or butyl radicals, and the alkoxy groups may be, for example methoxy, ethoxy or propoxy radicals.

The present invention also provides acid addition salts especially physiologically tolerable acid addition salts of compounds of the formula I with suitable mineral or organic acids. Among the acids which may be used to form these salts, there may be mentioned, for example, in the mineral series: hydrochloric, hydrobromic, sulfuric and phosphoric acids, and in the organic series: acetic, propionic, maleic, fumaric, tartaric, citric, oxalic, benzoic and methane-sulfonic acids.

The present invention provides a process for preparing the compounds of the formula I which comprises reacting a phenoxyaniline of the formula

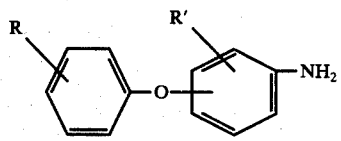

in which R and R' have the meanings given above, with a bis-(β-haloethyl)amine of the formula

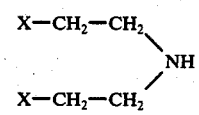

in which X is an halogen atom, for example a fluorine, chlorine or bromine atom, and alkalizing the resulting hydrohalide.

Such a process is advantageously carried out by heating under reflux the compounds II and III, which are known products, in a solvent, for example a low molecular weight alcohol such as methanol, ethanol or the like.

When the resulting hydrohalide crystallizes from the reaction mixture, it can be first isolated and used as such or transformed into the corresponding base by means of an alkaline agent. In contrast, if the hydrohalide remains in solution in the reaction mixture, the latter can be alkalized in order to liberate the free base of the general formula I.

The compounds of the formula I and physiologically tolerable acid addition salts thereof possess valuable pharmacological and therapeutic properties, especially glucid — and lipid — metabolism regulating properties. They may, therfore, be used as medicines, especially in the prevention and treatment of glucid — and lipid-metabolism disorders such as hyperlipidemia, obesity and arteriosclerosis.

Their toxicity is low and their $LD_{50}$ determined in mice varies from 200 to 1600 mg/kg by the oral route.

The activity of the compounds of the present invention on lipid-metabolism was evidenced in the rats submitted to different diets.

The compounds of the present invention were administered to rats receiving a lipid increased food, for a period of 4 days at daily doses which may vary from 12,5 to 50 mg/kg P.O. according to the compounds.

The animals were killed two hours after the last administration. There was then observed a decrease of the plasma triglycerides level up to 92% by comparison with untreated animals.

Similarly, the compounds of the present invention were administered to rats receiving a 2% cholesterol diet, for a period of 4 days at a dayly dose of 5 mg/kg P.O.

The animals were killed two hours after the last administration and there was then observed a decrease of the plasma cholesterol level up to 37% by comparison with intreated animals.

Furthermore and inhibiting activity on lipoproteinlipase of adipose tissue was evidenced in vitro for the compounds of the present invention which gave up to 35% of inhibition at a 0.00001 molar concentration.

The present invention also provides pharmaceutical compositions containing as active ingredient a compound of the formula I or a physiologically tolerable salt thereof, in admixture or conjunction with a pharmaceutically suitable carrier, such for example as distilled water, glucose, lactose, starch, talc, magnesium stearate, ethyl cellulose or cocoa butter.

The so-obtained pharmaceutical compositions are advantageously in unit dosage form and may contain from 100 to 300 mg of the active ingredient. They may be in form of tablets, dragees, capsules, suppositories or injectable or drinkable solutions and administered by oral, rectal or parenteral route at a dose of 100 to 300 mg 1 to 3 times a day.

The following examples illustrate the invention, the parts being by weight and the melting points being determined on a Kofler hot plate.

EXAMPLE 1

1-(4-phenoxyphenyl)-piperazine

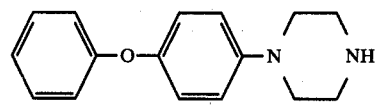

To a solution of 62.4 parts of bis-(β-bromoethyl)amine dihybromide in 160 parts of methanol there were added 37 parts of para-phenoxyaniline. The mixture was refluxed for 10 hours. 10.6 parts of $Na_2 CO_3$ were then added and the reaction mixture was refluxed for a further 10 hours. After cooling, the precipitate was filtered off, washed with 80 parts of methanol and dried.

There was obtained 29.5 parts of 1-(4-phenoxyphenyl)-piperazine monohydrobromide, M.P. 247° C.

EXAMPLE 2

1-(3-phenoxyphenyl)-piperazine

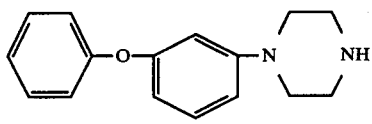

In the manner described in example 1 starting from 49 parts of meta-phenoxyaniline and 83.3 parts of bis-(β-bromoethyl)amine dihydrobromide there was obtained a clear solution. After evaporation of the solvent in vacuo, the residue was treated with 700 part of water, rendered alkaline with 60 parts of concentrated NaOH and extracted twice with 200 parts of ether. Th solution was dried. Upon distillation, there were obtained 26 parts of 1-(3-phenoxyphenyl)-piperazine, B.P./0.5 mm Hg: 180°–190° C.

To 11 parts of this base dissolved in 80 parts of anhydrous isopropanol, there were added 8.3 parts of methanesulfonic acid. After 4 hours, the resulting precipitate was filtered off, washed and dried. There were obtained 12.7 parts of 1-(3-phenoxyphenyl)-piperazine dimethanesulfonate, M.P.: 159° C.

EXAMPLES 3 to 20

In accordance with the procedures described in Example 1, but in place of utilizing as starting material, para-phenoxyaniline, there is used 2-phenoxyaniline, 4-(4-chlorophenoxy) aniline, 4-(3-chlorophenoxy) aniline, 3-chloro-4-phenoxy-aniline, 3-trifluoromethyl-4-phenoxy aniline, 4-(3-trifluoromethylphenoxy) aniline, 4-(4-methoxyphenoxy) aniline, 4-(4-bromophenoxy) aniline, 4-(4-methylphenoxy) aniline, 3-chloro-4-(4-methoxyphenoxy) aniline, 3-chloro-4-(3-trifluoromethylphenoxy) aniline, 3-phenoxy-4-trifluoromethoxyaniline, 3-phenoxy-4-trifluoromethylthio aniline, 4-(4-methylthiophenoxy) aniline, 4-(4-methoxy carbonylphenoxy) aniline, 3-ethoxycarbonyl-4-phenoxy aniline, 3-dimethylsulfamoyl-4-phenoxy aniline, and 4-(4-nitrophenoxy) aniline, thus there is obtained the corresponding 1-(2-phenoxyphenyl)-piperazine, M.P. 150° C (as monomethane-sulfonate, recryst. from isopropanol), 1-[4-(4-chlorophenoxy)-phenyl]-piperazine, M.P. 86°–87° C (recryst. from cyclohexane), 1-[4-(3-chlorophenoxy)-phenyl]-piperazine, 1-(3-chloro-4-phenoxyphenyl)-piperazine, M.P. 232°–233° C (as monohydrobromide, recryst. from ethanol), 1-(3-trifluoromethyl-4-phenoxy-phenyl)-piperazine, 1-[4-(3-trifluoromethylphenoxy)-phenyl]-piperazine, 1-[4-(4-methoxphenoxy)-phenyl]-piperazine, M.P. 221°–222° C (as monohydrobromide, recryst. from ethanol), 1-[4-(4-bromophenoxy)-phenyl]-piperazine, M.P. 268°–270° C, (as monohydrobromide, recryst. from acetic acid), 1-[4-(4-methylphenoxy)-phenyl]-piperazine, M.P. 205°–206° C, (as monohydrobromide, recryst. from ethanol), 1-[3-chloro-4-(4-methoxy-phenoxy-phenyl]-piperazine, 1-[3-chloro-4-(3-trifluoromethylphenoxy)-phenyl]-piperazine, 1-(3-phenoxy-4-trifluoromethoxy-phenyl)-piperazine, 1-(3-phenoxy-4-trifluoromethylthiophenyl)-piperazine, 1-[4-(4-methylthiophenoxy)-phenyl]-piperazine, M.P. 232°–234° C (as monohydrobromide, recryst. from dimethylformamide), 1-[4-(4-methoxycarbonylphenoxy)-phenyl]-piperazine, M.P. 242°–243° C (as monohydrobromide, recryst. from methanol), 1-(3-ethoxycarbonyl-4-phenoxy phenyl)-piperazine, M.P. 180° C (as monohydrobromide, recryst. from isopropanol), 1-(3-dimethylsulfamoyl-4-phenoxy phenyl)-piperazine, M.P. 242° C (as monohydrobromide, recryst. from ethanol) and 1-[4-(4-nitrophenoxy)-phenyl] piperazine.

Due to their pharmacological activity, the most interesting compounds are the compounds of formula I wherein R and R' which are the same or different are each selected from the group consisting of a hydrogen atom, a halogen atom, an alkoxy and a alkylthio radical each having from 1 to 5 carbon atoms inclusive.

Among this group the values hydrogen, chloro, bromo, methoxy and methylthio are particularly interesting as meanings of R and R'.

We claim:

1. A compound of the formula

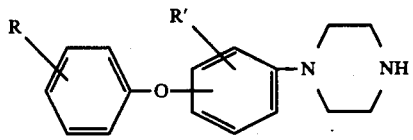

wherein R and R', which are the same or different, are each selected from the group consisting of hydrogen, halogen, alkyl, alkoxy and alkylthio each having from 1 to 5 carbon atoms inclusive, nitro, trifluoromethyl, trifluoromethylthio, trifluoromethoxy, alkoxycarbonyl wherein alkoxy has from 1 to 5 carbon atoms inclusive and dimethylsulfamoyl; or physiologically tolerable acid addition salts thereof.

2. A compound of claim 1 wherein R and R', which are the same or different, are each selected from the group consisting of hydrogen, halogen, alkoxy and alkylthio each having from 1 to 5 carbon atoms inclusive, or physiologically tolerable acid additions salts thereof.

3. A compound of claim 1 wherein R and R', which are the same or different, are each selected from the group consisting of hydrogen, chloro, bromo, methoxy and methylthio, or physiologically tolerable acid addition salts thereof.

4. A compound of claim 1 which is 1-(4-phenoxyphenyl)-piperazine.

5. A compound of claim 1 which is 1-[4-(4-methoxyphenoxy)-phenyl]-piperazine.

6. A compound of claim 1 which is 1-[4-(4-methylthiophenoxy)-phenyl]-piperazine.

7. A pharmaceutically administerable dosage unit for the treatment of a living animal body afflicted with lipid-metabolism disorders containing from 100 to 300 mg of a compound of claim 1 and a suitable pharmaceutically acceptable carrier.

8. A method for treating a living animal body afflicted with lipid-metabolism disorders, comprising the step of administering an amount of a compound of claim 1 which is effective for the alleviation of the said conditions.

* * * * *